(12) United States Patent
Schuhmacher et al.

(10) Patent No.: US 9,724,275 B2
(45) Date of Patent: Aug. 8, 2017

(54) DISPERSIONS OF NANOSCALE DENTAL GLASS PARTICLES AND METHODS FOR PREPARING THE SAME

(71) Applicant: Schott AG, Mainz (DE)

(72) Inventors: Joerg Schuhmacher, Mainz (DE); Jochen Herrmann, Mainz (DE); Hans-Joachim Schmitt, Ockenheim (DE); Bastian Schoen, Landshut (DE); Jens Suffner, Landshut (DE)

(73) Assignee: SCHOTT AG, Mainz (DE)

( * ) Notice: Subject to any disclaimer, the term of this patent is extended or adjusted under 35 U.S.C. 154(b) by 125 days.

(21) Appl. No.: 14/158,685

(22) Filed: Jan. 17, 2014

(65) Prior Publication Data
US 2014/0206791 A1    Jul. 24, 2014

(30) Foreign Application Priority Data

Jan. 18, 2013  (DE) .................. 10 2013 100 546

(51) Int. Cl.
*A61K 6/08* (2006.01)
*A61K 6/00* (2006.01)
*A61K 6/083* (2006.01)

(52) U.S. Cl.
CPC ............ *A61K 6/083* (2013.01); *A61K 6/0008* (2013.01); *A61K 6/0091* (2013.01)

(58) Field of Classification Search
CPC ...... A61K 6/00; A61K 6/0047; A61K 6/0052; A61K 6/007; A61K 6/0073; A61K 6/0088; A61K 6/02; A61K 6/0235; A61K 6/0255; A61K 6/0265; A61K 6/08; A61K 6/083
See application file for complete search history.

(56) References Cited

U.S. PATENT DOCUMENTS

| 4,375,967 | A | * | 3/1983 | Schaefer | .................. C08K 3/34 |
| | | | | | 106/35 |
| 4,567,030 | A | * | 1/1986 | Yuasa | ...................... B01J 20/10 |
| | | | | | 106/35 |
| 5,192,815 | A | | 3/1993 | Okada et al. | |
| 5,609,675 | A | * | 3/1997 | Noritake | ............... C04B 14/062 |
| | | | | | 106/35 |

(Continued)

FOREIGN PATENT DOCUMENTS

| CN | 1984632 | 6/2007 |
| DE | 19643781 A1 | 4/1998 |

(Continued)

OTHER PUBLICATIONS

Item 3 V-116-1130, Barium Silicate Glass datasheet from ESSTECH, Inc. (2015) [online]. Retieved online on Sep. 21, 2015. Retrived from internet <URL://http://catalog.esstechinc.com/item/glass-fillers/barium-silicate-glasses/item-1042?>.*

(Continued)

*Primary Examiner* — Sanza McClendon
(74) *Attorney, Agent, or Firm* — Ohlandt, Greeley, Ruggiero & Perle, L.L.P.

(57) ABSTRACT

Provided are a dispersion of a nanoparticulate mixed oxide of $SiO_2$ with at least one further metal oxide in a matrix monomer, methods for preparing such a dispersion, a dental composite producible by curing such a dispersion, and uses of the dispersion as a precursor for dental composites.

27 Claims, 4 Drawing Sheets

(56) References Cited

U.S. PATENT DOCUMENTS

| | | | |
|---|---|---|---|
| 6,106,606 | A | 8/2000 | Gellermann et al. |
| 7,335,250 | B2 | 2/2008 | Burtscher et al. |
| 7,963,769 | B2 * | 6/2011 | Qian .................. A61K 6/0029 433/228.1 |
| 2005/0252414 | A1 | 11/2005 | Craig |
| 2009/0093563 | A1 * | 4/2009 | Qian .................. A61K 6/0029 522/79 |

FOREIGN PATENT DOCUMENTS

| | | |
|---|---|---|
| DE | 102006045628 A1 | 4/2008 |
| JP | H02134307 A | 5/1990 |
| JP | 2006219439 A | 8/2006 |
| WO | 2005075348 A1 | 1/2005 |

OTHER PUBLICATIONS

Item 3 X-950-0000, BisGMA from ESSTECH, Inc (2015) [online]. Retrieved online on Sep. 21, 2015. Retrieved from internet <URL// :http://catalog.esstechinc.com/item/oligomers/bisgma/x-950-0000.*

German Office Action dated Sep. 13, 2013 corresponding to German Patent App. No. 10 2013 100 546.2 with English Translation.

Wei, et al.,"Novel Organic-Inorganic Chemical Hybrid Fillers for Dental Composite Materials"; Journal of Applied Polymer Science, vol. 70, pp. 1689-1699, 1998, 11 pp.

Guo Musun., Fluidization Handbook, 1st edition, p. 130, chemical industry publishing house, Jan. 31, 2008, with English translation, 7 pages.

* cited by examiner

Fig. 5
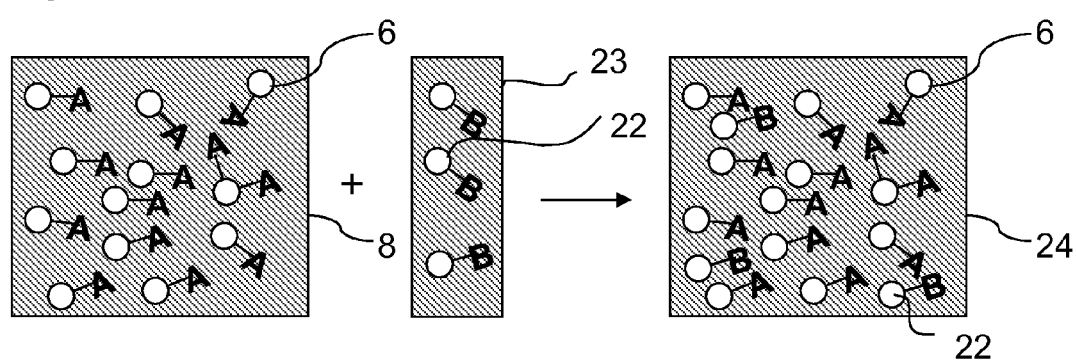
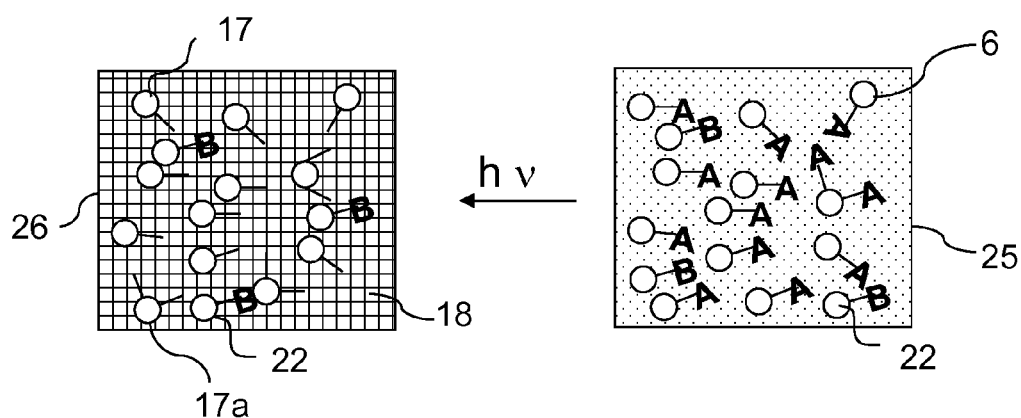

DISPERSIONS OF NANOSCALE DENTAL GLASS PARTICLES AND METHODS FOR PREPARING THE SAME

CROSS REFERENCE TO RELATED APPLICATIONS

This application claims benefit under 35 U.S.C. §119(a) of German Patent Application No. 10 2013 100 546.2, filed Jan. 18, 2013, the entire contents of which are incorporated herein by reference.

BACKGROUND OF THE INVENTION

1. Field of the Invention

The invention relates to a dispersion of a nanoparticulate mixed oxide of $SiO_2$ with at least one further metal oxide in a matrix monomer, to a dental composite with the dispersion as a precursor and obtainable by curing the dispersion, and to the use of the dispersion of the invention as a precursor for dental composites. The invention further relates to a method for preparing such a dispersion.

2. Description of Related Art

Dental composites are composite materials comprising a polymeric organic phase, in particular a resin matrix, and fillers materials, with preferably inorganic particles being used as a filler material. A dispersion of filler materials in a monomer is used as a precursor for such a dental composite. The precursor is provided in liquid or paste form, i.e. the filler particles are incorporated into a liquid organic phase. The liquid organic phase includes monomers which may be transformed into the resin matrix by polymerization. The corresponding dental composite is formed by curing the dispersion, i.e. by polymerization of the monomers. The physical properties of the dental composite are primarily determined by the type and proportion of inorganic filler materials and the shape, size, and size distribution thereof. By using a suitable filler material, adverse effects such as polymerization shrinkage of the matrix or water absorption thereof may be compensated for or mitigated.

Also, a suitable filler material may reduce the thermal expansion coefficient of the composite. At the same time, compressive strength, tensile strength, bending strength and abrasion resistance as well as the elastic modulus of the composite may be adjusted. These effects correspond with the content of filler material in the composite.

When using the dispersion as a precursor for dental composites, e.g. for a dental filling, polymerization of the monomers is usually induced by light in the visible or UV range. In terms of mechanical properties, in particular longevity of the fillings, a highest possible degree of polymerization throughout the entire volume of the filling is desired. Therefore it will be advantageous, in particular for polymerization of deep fillings, i.e. fillings with a comparatively large layer thickness, if the composite material exhibits high transmittance in the visible range. Scattering loss which may be caused by scattering at rather large filler particles, for example, or by different refractive indices of the filler material and the matrix, will adversely affect translucency.

At the same time, the composite material is desired to be as opaque as possible for X-rays, i.e. the material should have a high X-ray opacity to permit diagnosis using X-rays.

The first commercially available dental composites contained ground glass powders as a filler material. Average grain size was between 50 and 100 µm. However, the size of these macrofillers caused high abrasion. Glass chips broken out from the filling caused craters in the surface of the filling, and, moreover, the broken out glass chips acted as emery and thus increased abrasion of the filling.

By combining fumed silica as a nanofiller and ground glass particles as a microfiller, so-called hybrid fillers can be obtained which allow for a higher solids content in the composite. This makes it possible to obtain composites that exhibit good polishability, high abrasion resistance, and good mechanical strength.

Conventional melting and grinding processes allow to obtain glass powders with particle sizes of less than 1 µm. A drawback of this preparation method, however, is that in addition to components providing for the functional properties, in particular refractive index and X-ray opacity of the filling body, the glass composition also comprises components which ensure meltability in a technically relevant range and which suppress crystallization. However, this will generally involve an increase in the refractive index of the material, thereby restricting, in terms of type and proportion, the choice of components relevant for X-ray opacity, which for their part also cause an increase in refractive index of the material. Furthermore, the preparation of glass powders or glass particles in nanoscale form, i.e. having a particle diameter of less than 100 nm, is generally not economically efficient, due to the grinding times required. Moreover, in particular with long grinding times, there is always a risk that the materials leach out during the grinding process and thus lose their desired properties.

Patent document EP 1 711 433 B1 (WO2005/075348), by contrast, describes dental composites comprising a mixed oxide of $SiO_2$ obtainable by flame spray pyrolysis, and at least one further oxide of any of the elements of a group including Y, La, Ta, Ce, Pr, Nd, Sm, Eu, Gd, Tb, Dy, Ho, Er, Tm, Yb, and Lu, as an X-ray opaque component. However, the corresponding dental composites only exhibit a comparatively low X-ray opacity and poor transparency for light in the visible range.

Published patent application DE 10 2006 045 628 A1 also discloses composite materials including at least one nanoparticulate mixed oxide comprising $SiO_2$ and an oxide of any of elements Y, La, Ta, Ce, Pr, Nd, Sm, Eu, Gd, Tb, Dy, Ho, Er, Tm, Yb, and Lu. However, due to the great difference in the refractive indices of filler materials and matrix, poor transparency has to be expected here likewise.

Instead of the preparation methods for fillers mentioned above, inorganic fillers may also be prepared by chemical precipitation. For example, patent document DE 196 43 781 C2 describes preparation of X-ray opaque spherical particles via a sol-gel route. The particles so obtained include $SnO_2$ and at least one further oxide of the elements of the $1^{st}$ through $5^{th}$ main group and/or of the transition metals. However, mandatorily, the particles include $SnO_2$.

Furthermore described in the literature (Wei et al., Journal of Applied Polymer Science, 70, 1689-1699 (1998)) is the preparation of a filler material based on $SiO_2$ using a sol-gel process. In this filler material, polymer chains are covalently bound to the silicon network. In form of a composite with the appropriate matrix monomer, the filler material so obtained exhibits enhanced compressive strength, however, the composite does not include any components to increase radiopacity.

SUMMARY

An object of the present invention, therefore, is to provide dispersions of filler particles in a monomer as precursors for translucent dental composites on the basis of nanoscale, X-ray opaque filler materials, as well as the corresponding dental composites. It is in particular desired that the composites of the invention have advantageous physical-mechanical properties as compared to the prior art. Another object of the invention is to provide a suitable method for preparing the dispersions and composite precursors of the invention.

The dispersions according to the invention comprise a filler material and at least one monomer. These dispersions will also be referred to as a composite precursor below. The monomer has at least one polymerizable group. By polymerization of the monomer, a matrix is formed. Depending on the monomer used, the polymerization can be a radical or a cationic polymerization of vinylic double bonds, for example. The curing of the composite may also be accomplished by a cationic ring-opening polymerization.

In particular, the monomer may be polymerized by irradiation of light. For this purpose, an initiator may additionally be added to the dental composite.

The filler material included in the dental composite has a nanoscale structure. Preferably, the particles of the filler material have a spherical or at least substantially spherical structure, which results in a very good polishability in the application case. For example, with spherical particles there is a much lower risk for these particles to break out of the composite surface during the polishing process than it is the case with particles having sharp edges such as obtained, for example, by grinding glass. A breaking out of the filler particles from the polymer matrix, however, will lead to a formation of craters which in turn constitute preferred attachment sites of plaque. Therefore, the composites according to the present invention are superior to corresponding composites with sharp-edged particles, in terms of abrasion resistance and polishability.

The filler material is a mixed oxide which in addition to silicon includes at least one metal M in oxidic form. The metal M has an atomic number of greater than 36 and is opaque to X-rays. By using an appropriate mixed oxide, therefore, an X-ray opaque filler material can be obtained.

Particularly advantageously, by selecting an appropriate metal M and its quantitative proportion in the mixed oxide not only a desired radiopacity can be adjusted but at the same time also the refractive index of the filler particles. The refractive index is brought to the desired value alone by adding the X-ray opaquer. Unlike dental glasses which are produced by conventional melting and grinding routes, the filler materials according to the invention do not include any additional oxide components that have to be added for manufacturing reasons (for example to increase meltability) and which, though increasing the refractive index, do not contribute to X-ray opacity. Thus, the filler materials of the invention may have a high X-ray opacity without departing from the advantageous range of refractive indices predetermined by the matrix.

Preferably, the refractive index of the filler material is adjusted so as to substantially correspond to the refractive index of the matrix monomer. If the matrix monomer and the filler material have similar or substantially the same refractive indices, this will have a positive effect on the transparency of the composite. A high degree of transparency of the composite has an advantageous effect on homogeneity of polymerization within the filling and on the degree of polymerization. Furthermore, high transparency is beneficial to the aesthetic appearance of the composite. Preferably, a difference between the refractive index of the filler material and the refractive index of the matrix monomer is less than 0.1, more preferably less than 0.05, and most preferably less than 0.02. In one embodiment, the polymer matrix has a refractive index in a range from 1.51 to 1.7, preferably in a range from 1.53 to 1.55.

The particles of the filler material according to the invention, also referred to as mixed oxide particles below, further exhibit a surface functionalization. At least one polymerizable group on the surface of the filler particle or mixed oxide particle is covalently bound thereto. The polymerizable group can polymerize under the same conditions as the matrix monomers and will form a copolymer therewith. Thus, copolymerization of the matrix monomer and the filler material will produce a permanent chemical bond between the matrix and the filler material. In addition, the surface functionalization of the filler materials results in a good dispersibility of the filler materials in the matrix monomer and thus in a uniform distribution of the filler particles in the dispersion. This uniform distribution and the covalent bond between cured matrix and filler material increases the mechanical strength of the composite. Preferably, the solids content of the dispersion ranges from 10 to 70 wt %, more preferably from 20 to 60 wt %, and most preferably from 30 to 50 wt %.

According to one advantageous embodiment of the invention, the mixed oxide of the filler material is a binary mixed oxide according to the formula $SiO_2$—$MO_x$, wherein the metal M is X-ray opaque. X-ray opacity and refractive index of the mixed oxide may be adjusted by the type and proportion of metal M in the mixed oxide. In a modification of the invention, a ternary mixed oxide according to the formula $SiO_2$-$MO_x$-$M^TO_y$ is provided as a filler material, with metals M and $M^T$. The two metals M and $M^T$ are X-ray opaque metals having an atomic number of greater than 36, i.e. opaquers, wherein the content of the two opaquers in the filler material may be different. By virtue of the use of two different opaquers which are furthermore different in terms of their contribution to the refractive index, additional parameters are available for adjusting refractive index and radiopacity. Preferably, metals M and $M^T$ are selected from a group of elements including Ba, Sr, La, Cs, Sn, Zr, Yb, Y, Ta, Ce, Pr, Nd, Sm, Eu, Gd, Tb, Dy, Ho, Er, Tm, Lu, Bi, more preferably from the group of elements Ba, Sr. Particularly preferably, metals M and $M^T$ are barium and/or strontium.

It has been found to be particularly advantageous to introduce the polymerizable group using an appropriately functionalized silane.

Preferably, the mixed oxide particles exhibit a degree of modification with copolymerizable groups from 0.001 to 1.5, more preferably from 0.01 to 0.7. The degree of modification $M_1$ with copolymerizable groups, in the context of the invention, refers to the molar ratio of copolymerizable group to the inorganic part of the mixed oxide particle (corresponding to the amounts of silicon and the metal M, or metals M and $M^T$), in particular to the ratio of quantities n $M_1$=n(copolymerizable groups)/n(Si)+n(M); or $M_1$=n(copolymerizable groups)/n(Si)+n(M)+n($M^T$).

In one embodiment, the dispersion comprises further components. These may for example include initiators, colorants, or stabilizers.

Preferably, acrylates are employed, in particular methacrylates such as e.g. methyl, ethyl, butyl, benzyl, furfuryl, or phenyl (meth)acrylate, and 2-hydroxyethyl or propyl (meth)acrylate, or mixtures of different acrylates. Besides monofunctional monomers, multi-functional monomers may be used, for example, but not limited to, bisphenol A di(meth)acrylate, bis-GMA, ethoxylated bisphenol A di(meth)acrylate, UDMA, di-, tri-, or tetraethylene glycol di(meth)

acrylate, trimethylolpropane tri(meth)acrylate, pentaerythritol tetra(meth)acrylate, and butanediol di(meth)acrylate, 1,10-decanediol di(meth)acrylate, or 1,12-dodecanediol di(meth)acrylate. The use of bis-GMA has been found to be particularly advantageous. That is, composites with a matrix based on bis-GMA exhibit significantly less pronounced polymerization shrinkage than for example composites with MMA as the matrix monomer. It is also possible to use mixtures of different methacrylates. By combining bis-GMA with a low viscosity methacrylate as a co-monomer, for example, the overall viscosity of the matrix monomers may be decreased, which has a particularly favorable effect on the ratio of polymerization. For example, bis-GMA may be used in combination with TEG-DMA.

According to another embodiment, the monomer and filler particles include epoxides as a polymerizable group.

By copolymerization of the functionalized filler material and the matrix monomers, the matrix and the filler material are covalently linked together. In one embodiment of the invention, the filler material is functionalized with a silane which carries a side chain based on acrylate, in particular methacrylate, e.g. 3-methacryloxypropyltrimethoxysilane (MPTMS).

According to another modification of the invention, the mixed oxide particles are additionally functionalized with organic residues which do not have copolymerizable groups. In one embodiment of the invention, the particles have organic aliphatic residues or side chains. In particular alkyltrialkoxysilanes may be used, such as alkyltrimethoxysilanes, alkyltriethoxysilanes, and appropriate mixtures. The appropriate alkyltrialkoxysilanes as a second silanization agent are preferably used in combination with a copolymerizable silane. The non-copolymerizable organic residues or side chains enhance flexibility of the overall system and thus counteract embrittlement and cracking of the cured composite. Moreover, the viscosity of the dispersion may be reduced and the pot life thereof may be significantly increased.

The degree of modification $M_2$ of the particles having non-copolymerizable organic side chains preferably ranges from 0.001 to 1.0, more preferably from 0.01 to 0.5, and can be defined as a molar ratio as follows, with n=quantity of substance, in mol:

$M_2$=n(non-polymerizable groups)/n(Si)+n(M); or $M_2$=n(non-polymerizable groups)/n(Si)+n(M)+n($M^T$).

In one embodiment of the invention, the filler particles have an average particle size from 5 to 100 nm, preferably from 10 to 70 nm, and more preferably from 20 to 50 nm. The small particle size of the filler material induces a high mechanical stability of the composite or of the filling formed therefrom. Furthermore, the small particle size avoids undesirable light scattering at the filler material and thus prevents turbidity effects in the composite.

According to one modification of the invention, the refractive index of the filler material is matched, via its composition, to the refractive index of the matrix monomer so closely that the difference between the refractive index of the filler material and the refractive index of the matrix monomer is less than 0.10, preferably less than 0.05, so that scattering loss is minimized. In particular, the composite exhibits a translucency of at least 30%, preferably at least 50%, more preferably at least 70% for light in the visible range. In particular, the composite has a transparency of at least 75%, in particular at least 85%, or even at least 90% for light in the visible range, in case of a solids content of at least 10 wt %.

X-ray opacity of the nanoscale fillers of the dispersion or of the composite obtained therefrom particularly preferably ranges from 50 to 1500% Al, more particularly even from 75 to 1000% Al, and most preferably from 100 to 800% Al.

Furthermore, the invention relates to a method for preparing a dispersion comprising a nanoscale mixed oxide as a filler material and a matrix monomer, by sol formation, especially as a precursor for a dental composite. In particular, a method is provided for preparing the dispersions according to the invention described above.

The preparation method of the invention comprises the following process steps:

a) preparation of particles in form of a colloidal solution by producing a sol;

b) functionalization of the particles;

c) cleaning of the reaction solution from undesired components;

d) redispersion of the functionalized particles in the matrix monomer;

e) processing of the particle/matrix monomer dispersion.

In step a), the nanoscale mixed oxide particles are prepared by producing a sol according to a sol-gel process, and the particles are provided in form of a sol. For this purpose, an organic silicon precursor, such as tetraalkoxysilane, is reacted with water in the presence of a metal salt $M_aX_b$, with a base used as a catalyst.

For this purpose, according to one embodiment, first a solution A is provided including a silicon precursor and a metal salt dissolved in a solvent, and a solution B is provided including a solvent and an aqueous basic solution. In addition, one of the two solutions includes a sol stabilizer. To start the reaction, solution A and solution B are mixed under convection. Preferably, solution B includes ammonia as the base. The solvent employed in solutions A and B is preferably a low boiling alcohol, such as ethanol, methanol, or isopropanol.

During the hydrolysis of the precursors accomplished in this manner, a corresponding sol is formed.

The metal M is an X-ray opaque metal, i.e. metal M has an atomic number of greater than 36. The metal precursor used reacts to form the metal oxide $MO_x$ included in the mixed oxide.

When a precursor $M_aX_b$ is used, the mixed oxide particles will have a composition of $SiO_2$-$MO_x$, with varying proportions of $SiO_2$ and $MO_x$, and will be X-ray opaque.

As the precursors for forming metal oxides $MO_x$, the respective metals are used in form of metal salts of the form $M_aX_b$, or of hydroxides, instead of metal alkoxides which are often very sensitive to air and moisture. On the one hand, this simplifies the reaction regime, since particle formation does not have to be accomplished under protective gas. Furthermore, the metal salts are usually available at lower cost, and moreover they exhibit good solubility in the employed solvents.

In one embodiment of the invention, the corresponding metal perchlorates are used as a precursor. In particular barium and strontium perchlorate exhibit good solubility in the employed solvents.

In another embodiment, metal hydroxides are used as the precursors. In this case, they are neutralized, at least partially, by adding acids, in particular by adding methacrylic acids. The partially neutralized solutions have a weak alkaline pH. Depending on the acid used, the metal hydroxides may also be completely neutralized.

Furthermore, a sol stabilizer for stabilization of the sol is used in step a).

By introducing a further oxide into the silicate material system, in particular a basic oxide, the zero-crossing of the zeta potential shifts to a pH of 8 to 9, while the zero-crossing for pure $SiO_2$ is at a pH of 2. However, since the particle synthesis takes place at pH values from 8 to 9, in the case of mixed oxide particle synthesis this results in that the particles formed in the process are substantially free of surface charge and strongly tend to agglomerate, since now no repulsive electrostatic interactions are effective between the particles, but only attractive van der Waals forces. However, by using a sol stabilizer, a formation of agglomerates and thus a formation of a precipitate is avoided, due to a steric stabilization of the particles. Thus, a colloidal solution is obtained during particle synthesis, which may be transformed, by the subsequent steps, into a nanoparticle-filled matrix monomer dispersion.

Sol stabilizers that may be used include sterically demanding silanes, i.e. silanes having a sterically demanding organic residue, or protective colloids. In one embodiment of the invention, hydroxypropylcellulose is used as a protective colloid. If silanes are used as sol stabilizers, particle formation and surface modification may be accomplished in a common step.

Further, due to the stabilization of the sol the precursor of the metal oxide component $MO_x$ is prevented from reacting too fast, and thus a segregation is avoided, i.e. a separate formation of $SiO_2$ particles and $MO_x$ particles. That is, only by using a suitable sol stabilizer, the formation of a mixed oxide particle is made possible.

Due to the synthesis conditions as chosen in step a), the formation of the mixed oxide particles is accomplished in self-organizing manner. Preferably, ammonia or an ammonia solution is used as the base in step a). In this manner, the particles form into a spherical geometry during the synthesis, so that a separate rounding step as part of the overall preparation process may be dispensed with.

Moreover, only sol formation occurs during the particle synthesis, but not a gel formation. Therefore, no gelling step with subsequent drying and calcination is necessary to prepare the desired mixed particles. Thus, the overall preparation process can be simplified.

In gelling and calcination processes there is a risk that the particles agglomerate, aggregate, or sinter during relevant post-processing steps. The agglomerates or aggregates and sinter aggregates formed have to be broken up mechanically, with significant costs in terms of energy and time, and with nano-clusters possibly remaining, which may cause undesirable light scattering and hence turbidity effects.

In step b), surface functionalization of the mixed oxides is accomplished. For this purpose, a functionalized silane is added to the reaction solution provided in step a), after completion of particle formation. The silane in this case has polymerizable groups which may be copolymerized with the employed matrix monomer. Due to the introduction of the polymerizable group with a silane, surface modification occurs under formation of covalent bonds. According to one embodiment, silanes of the formula $ASiX_3$ or $ARSiX_2$ are employed, wherein X are hydrolyzable groups, and group A is a copolymerizable functional group. Optionally, the silane may furthermore comprise a non-hydrolysable organic residue R. Preferably, group X is selected from X=OR, halogen, $NR''_2$, with R''=alkyl, aryl.

If a sterically demanding silane is used as a sol stabilizer, the formation of particles and the surface modification thereof are accomplished in a common step.

Thus, a permanent chemical bond between the filler material and the matrix monomer is obtained by copolymerization of the polymerizable groups of the mixed oxide with the matrix monomer, which is particularly advantageous in terms of mechanical strength of the composite. Moreover, the surface modification of the mixed oxide particles results in a better dispersibility of the filler particles in the matrix monomer (step d).

The coupling of the silanization agent to the surface of the mixed oxide is performed under the same reaction conditions as the formation of particles in step a), so that no further processing steps or change in reaction conditions have to be carried out before the silane is added. Preferably, 3-methacryloxypropyltrimethoxysilane is employed as a silanization agent.

According to a modification of the invention, at least one further silane is additionally used for surface modification, with an organic non-copolymerizable residue, more preferably an aliphatic residue. Preferably used are silanes of the formula $RSiX_3$ or $RR^TSiX_2$, wherein X are hydrolyzable groups, and groups R and $R^T$ are non-hydrolyzable organic residues. Preferably, group X is selected from X=OR, halogen, $NR''_2$, with R''=alkyl, aryl.

Other than when using metal alkoxides, if metal salts are used according to the invention the counter ion, or if metal hydroxides are used the conjugate base of the acid employed in step a) is obtained as an undesirable component or by-product which has to be separated.

According to step c) of the preparation method of the invention, the counter ion is merely separated by ion exchange. An ion exchange process surprisingly easily permits to replace the counter ion or the conjugate base by hydroxide ions. Thus, after step c), only the base added in solution B, e.g. ammonia, water, and the solvent used in step a) will be present as unwanted by-products which can be easily removed in a subsequent step e). In particular, the separation of the counter ion may accomplished by filtering the reaction solution through an ion exchange resin.

Since the employed matrix monomers are generally monomers which have a higher boiling point than the solvent used in step a), the particles may be dispersed into the matrix monomer from the sol prepared in this way.

Therefore, it is not necessary to remove the solvent before dispersing the filler material into the matrix monomer in step d), which could lead to agglomeration or aggregation of the filler particles. The removal of solvent, water, and base may thus be accomplished in step e), for example by distillative processes.

In this manner, a nanoparticle-filled matrix monomer dispersion is obtained, which may be used in its present form as a finished product, or as a base component in another formulation as a precursor for a dental filler. In addition, homogeneous distribution of the mixed oxide particles in the monomer is achieved by the preparation method according to the invention, which has a positive effect on the physical and mechanical properties of the cured composite. The ratio of filler material to the matrix monomer as a dispersant depends on the desired solids content of the composite.

According to one embodiment, acrylates are used as the matrix monomer, in particular methacrylates, such as bis-GMA, or TEG-DMA. The use of co-monomers is also possible. Through the type and amount of the employed co-monomers, both procedural parameters such as viscosity of the monomer matrix mixture, and the material properties of the polymerized composites may be influenced, for example.

The preparation method comprises preparation of a nanoparticle dispersion without passing through an intermediate powder stage. First, this offers the advantage that a formation of agglomerates which is unavoidable during powder production and especially pronounced for nanoparticles, and the related redispersion step can be avoided. Moreover, the safety technology required when handling nanoscale powders can be omitted.

The preparation method furthermore permits to adjust the refractive index of the mixed oxide $SiO_2$-$MO_x$ by choosing the type of the X-ray opaque metal and the amount of the metal precursor employed. This permits to match the refractive index of the filler material to the refractive index of the matrix monomer used. In this way, turbidity effects of the composite can be avoided, for example, and the optical properties thereof can be optimized.

Particularly advantageously, barium or strontium are used as the X-ray opaque metal, both in terms of X-ray opacity and matching of the refractive index, as well as in view of the handling of relevant precursors in the preparation process. Preferably used as a precursor is barium perchlorate, or barium hydroxide partially neutralized with a suitable acid.

Preparation of the dispersion is preferably performed as a one-pot synthesis. In this manner, the process engineering effort is minimized.

In a modification of the preparation method according to the invention, two metal precursors $M_aX_b$ and $M^T{}_cX_d$ of different metals M and $M^T$ are used. The ternary mixed oxide formed according to this modification has a composition according to the formula $SiO_2$-$MO_x$—$M^TO_y$, with varying proportions of the individual oxides. According to one embodiment, the ternary mixed oxide comprises silicon oxide, barium oxide, and strontium oxide.

Preferably, a silane of the formula $SiX_4$ is used as the silicon precursor, with 4 hydrolyzable groups X selected from a group of X=OR, halogen, $NR_2$ (R=alkyl, aryl), H, more preferably a tetraalkoxysilane selected from the group comprising tetramethylorthosilicate [TMOS, $Si(OCH_3)_4$], tetraethylorthosilicate [TEOS, $Si(OC_2H_5)_4$], tetrapropoxysilane [$Si(OC_3H_7)_4$], and/or a silane according to the formula $RSiX_3$ with 3 hydrolyzable groups X selected from a group of X=OR, halogen, $NR_2$ (R=alkyl, aryl), H, and with a non-hydrolysable organic side group R.

Preferred solvents are low-boiling alcohols, in particular ethanol.

The dispersions obtained in step e) may be used as a precursor for a dental composite. According to another embodiment, other components, such as initiators, other monomers, or filler particles are added to or mixed with the dispersions obtained in step e).

By polymerization the dispersions will cure into the corresponding composite. The dispersions may for example be used by being filled into dental cavities or by being applied to the tooth surface. Furthermore, the dispersions may be introduced into a mold and cured.

The invention will now be described with reference to the accompanying FIGS. 1 to 5 and by way of the illustrated exemplary embodiments.

BRIEF DESCRIPTION OF THE FIGURES

FIG. 5 schematically illustrates the transformation of a dispersion including additional functionalized mixed oxide particles into a dental composite.

DETAILED DESCRIPTION

Figure 1:
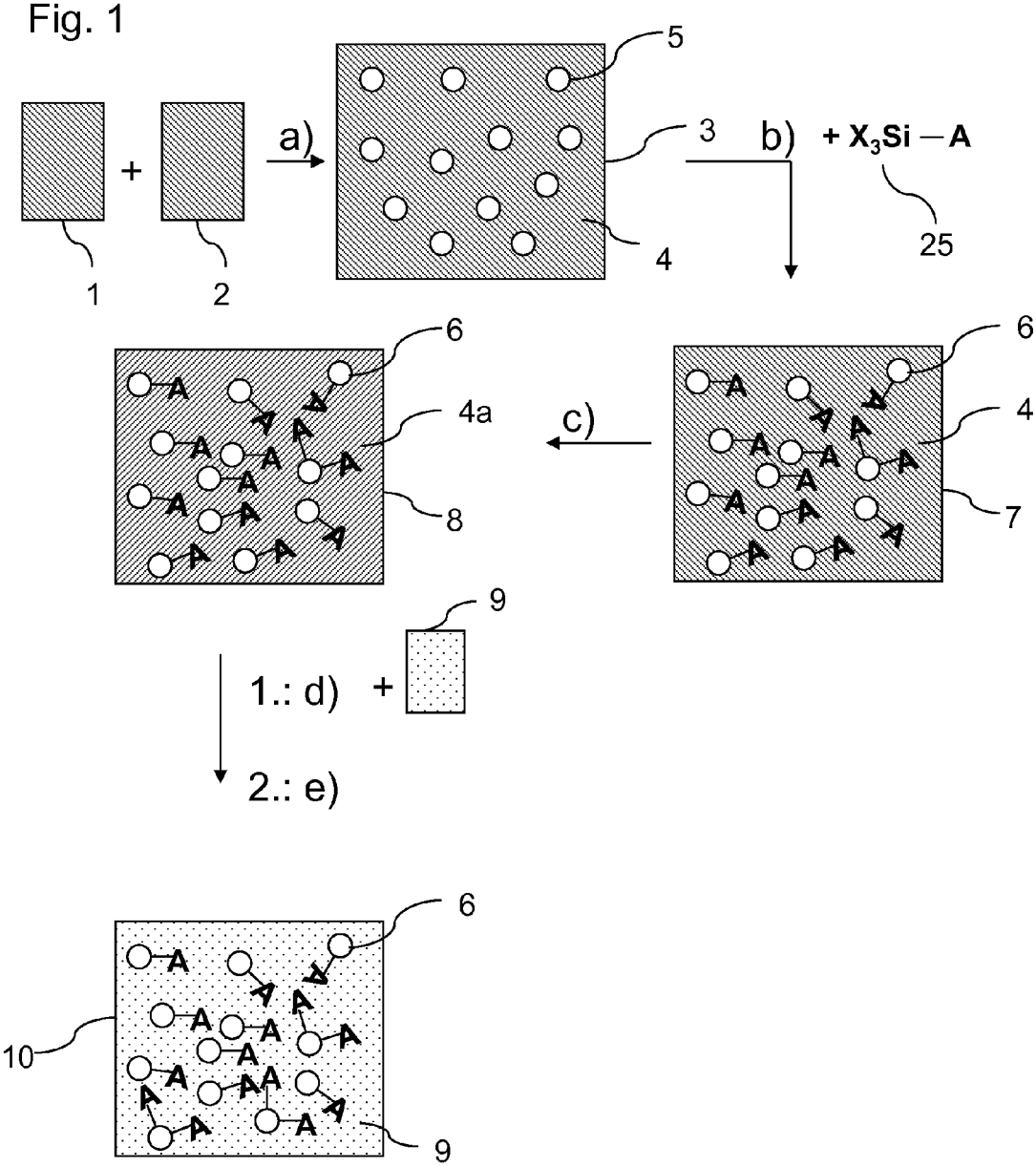
FIG. 1 schematically illustrates a first embodiment of the preparation method.

FIG. 1 schematically illustrates an embodiment of the inventive method for preparing a corresponding dispersion 10 of nanoscale mixed oxide particles 6 in a monomer matrix 9. In step a), first a sol 3 is formed. For this purpose, solutions 1 and 2 are mixed. Solutions 1 and 2 are the solutions A and B as described above, with solution 1 (solution A) including a silicon precursor and a salt of an X-ray opaque metal M, a sol stabilizer (not shown) and a solvent 4, and solution 2 (solution B) including an aqueous base (not shown) and also the solvent 4. The reaction mixture is stirred until particle formation is completed. The resulting sol 3 comprises nanoscale mixed oxide particles 5 in solvent 4, and further comprises undesired reaction products from step a) (not shown). In subsequent step b), surface modification of mixed oxide particles 5 is effected using a silane 25. In this embodiment, silane 25 has a formula $X_3SiA$, wherein functionality A is a group that is copolymerizable with the matrix monomer. Group X is a hydrolyzable group and is preferably selected from X=OR, halogen, $NR''_2$, with R''=alkyl, aryl.

The mixed oxide particles 6 so obtained have a covalently bound functionality A which is copolymerizable with the matrix monomer 9 added in step d). The degree of modification of the functionalized mixed oxide particles 6 may be adjusted through the amount of the silane 25 added in step b). In step c), undesired sol components are separated through a ion exchanger. The so conditioned sol 8 is redispersed in matrix monomer 9, in step d). Subsequently, solvent 4, water, and base (not shown) are removed to obtain the dispersion 10.

Figure 2:
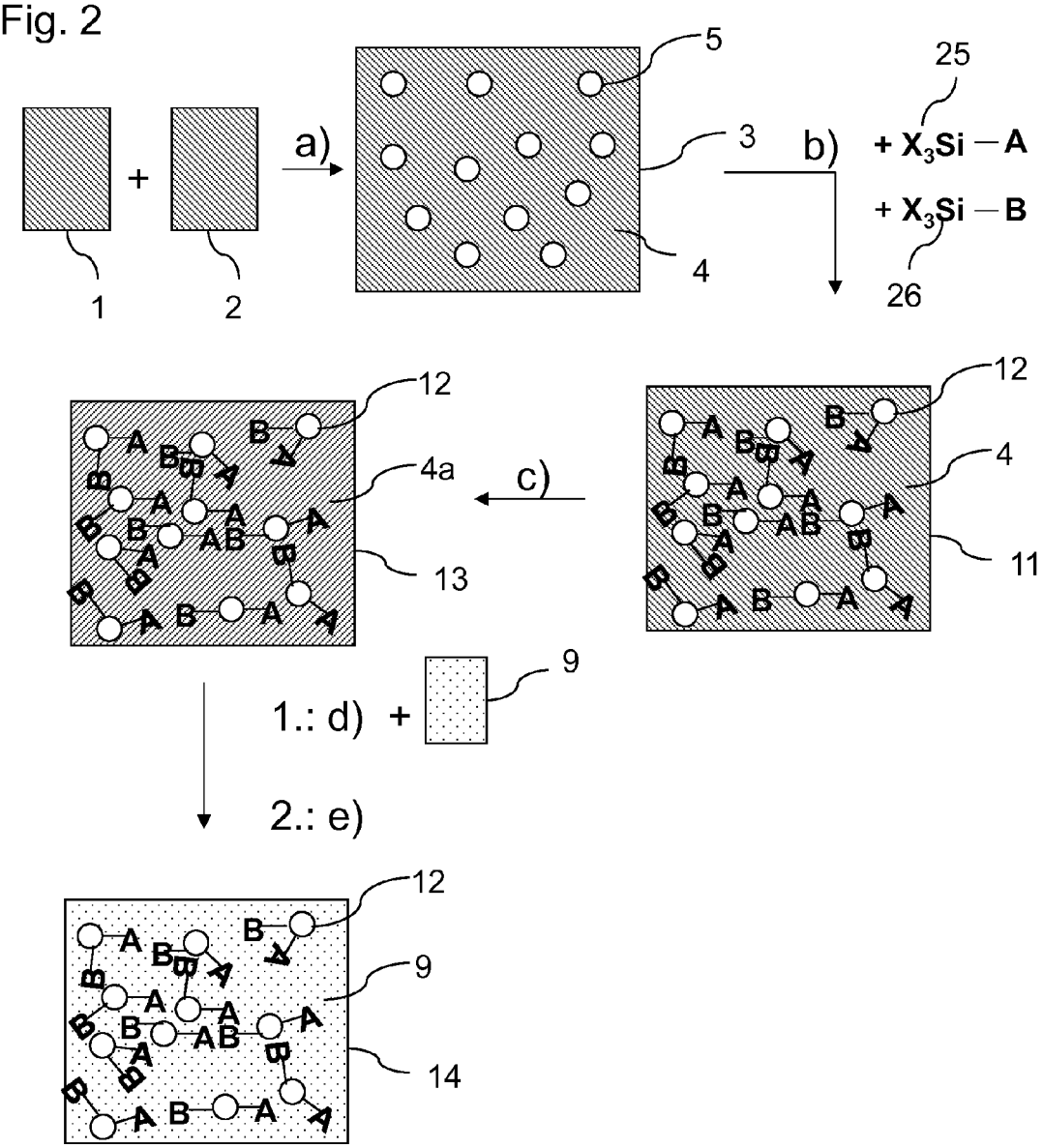
FIG. 2 schematically illustrates a second embodiment of the preparation method, in which the mixed oxide particles have a further surface modification, in addition to the copolymerizable group.

FIG. 2 schematically illustrates another embodiment of the preparation method. Here, in addition to the silane 25, a silane 26 having another, non-polymerizable functionality B is used in step b). Therefore, the mixed oxide particles 12 have functionalities B, in addition to copolymerizable groups A. Here, again, modification degrees may be adjusted through the amount of employed silanes 25 and 26.

Figure 3:
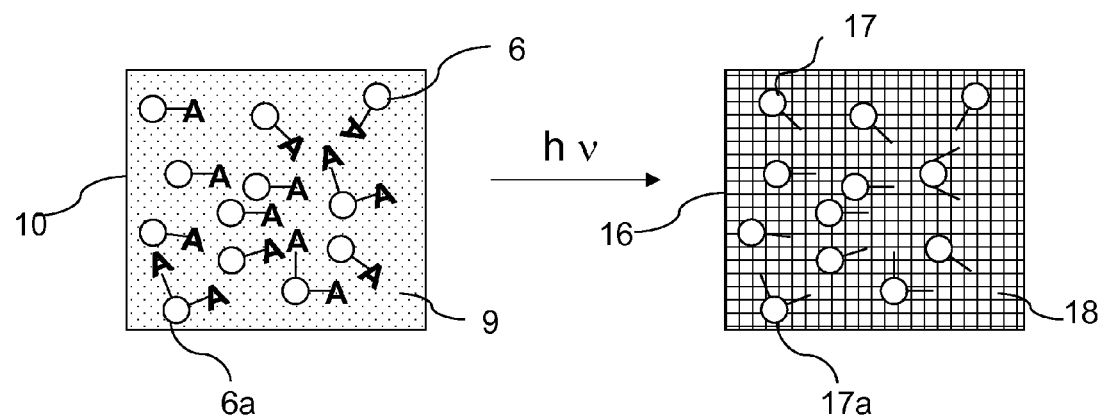
FIG. 3 schematically illustrates the transformation of the dispersion according to the invention into a dental composite.

FIG. 3 schematically illustrates the transformation of dispersion 10 according to the invention into a corresponding dental composite 16. By irradiating light of a suitable wavelength, polymerization of the matrix monomers 9 occurs, so that a resin matrix 18 is obtained. Here, copolymerization of matrix monomer 9 and functional groups A of mixed oxide particles 6 is accomplished, so that in dental composite 16 the mixed oxide particles 17 are covalently bound to the resin matrix 18. Depending on the degree of modification of the mixed oxide particles 6a, the latter may also act as a crosslinker 17a.

Figure 4:
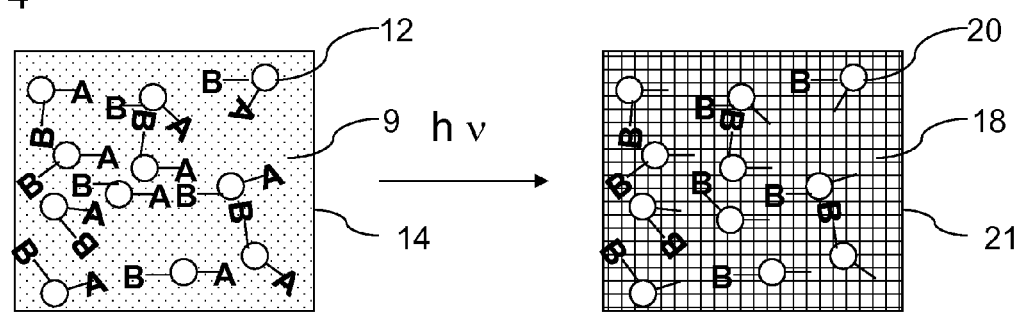
FIG. 4 schematically illustrates the transformation of the dispersion as prepared according to FIG. 2 into a dental composite.

FIG. 4 schematically illustrates the transformation of another embodiment of a nanoscale dispersion 14 into a corresponding dental composite 21. Mixed oxide particles 12 of the dispersion have, besides copolymerizable groups A, another functionality B which is not reactive under the polymerization conditions and therefore is also present in the cured dental composite 21. Thus, the physical and mechanical properties of dental composite 21 may be influenced by the group B of mixed oxide particles 12. For example, a modification of the mixed oxide particles with flexible side chains as a functionality B counteracts embrittlement of dental composite 21.

FIG. 5 schematically illustrates another possibility to improve flexibility of the dental composite. In this embodiment, further mixed oxide particles 22 are added to the sol 8 which includes mixed oxide particles 6 having a copolymerizable functionality A. The functional group B of the second mixed oxide particles 22 is not reactive under the reaction conditions of polymerization. Therefore, once the dispersion is cured, dental composite 26 comprises mixed oxide particles 17 covalently bound to the resin matrix, and functionalized mixed oxide particles 22 which are not covalently bound into the resin matrix 18.

Exemplary Embodiments

EXAMPLE 1

Dispersion of $SiO_2$—BaO Nanoparticles in a Bis-GMA/TEG-DMA Matrix Using Barium Perchlorate as a Precursor and Hydroxypropylcellulose as a Sol Stabilizer Step a): Particle Synthesis Solution A: 8 g of anhydrous barium perchlorate is dissolved in 238 ml of ethanol. To stabilize the solution, 1.2 ml of acetylacetone is added. Subsequently, 26.8 ml of TEOS is added to the solution.

Solution B: 278 ml of ethanol is mixed with 29 ml of a 25% $NH_4OH$ solution, and 3 g of hydroxypropylcellulose (HPC) is added as a sol stabilizer. The solution is stirred until the sol stabilizer dissolved.

To start the reaction, solution A is rapidly added to solution B with vigorous stirring. Subsequently, the reaction mixture is stirred for 24 h. As a result of particle formation, the solution gradually becomes turbid.

Step b): Surface Modification

For silanization of the particles synthesized in step a), 2.8 ml of 3-methacryloxypropyltrimethoxysilane (MPTMS) is added to the reaction solution. The reaction solution is stirred again for 24 hours.

Step c): Separation of the Counter Ion

To remove the perchlorate ions present in the reaction mixture, the solution is filtered through a column filled with 50 g of ion exchanger Lewatit M500 OH. The ion exchanger is loaded with hydroxide ions, so that during the filtration perchlorate ions are removed from the solution and are replaced by hydroxide ions.

Step d): Dispersing of the Particles in the Matrix Monomer 90 g of a mixture of bis-GMA and TEG-DMA with a mixing ratio of 1:1 are added to the reaction solution ion-exchanged in step c).

Step e): Processing of the Reaction Solution

Components ammonia, ethanol, and water present in the solution are removed from the mixture by vacuum distillation on a rotary evaporator. What remains is a 10% dispersion of silanized $SiO_2$—BaO nanoparticles with Bis-GMA/TEG-DMA as the matrix monomer.

EXAMPLE 2

Dispersion of $SiO_2$—BaO Nanoparticles with a Mixture of Bis-GMA/TEG-DMA as a Matrix Monomer Using 3-Methacryloxypropyltrimethoxysilane (MPTMS) as a Sol Stabilizer Steps a) and b): Particle Synthesis and Silanization Solution A: 8 g of anhydrous barium perchlorate is dissolved in 214 ml of ethanol. To stabilize the solution, 1.2 ml of acetylacetone is added. Then, 12.3 ml of TEOS is added to the solution. Subsequently, 13.1 ml of 3-methacryloxypropyltrimethoxysilane (MPTMS) is added to the solution.

Solution B: 252 ml of ethanol is mixed with 26 ml of a 25% $NH_4OH$ solution.

To start the reaction, solution B is rapidly added to solution A with vigorous stirring. Subsequently, the reaction mixture is stirred for 24 h. As a result of particle formation, the solution gradually becomes turbid.

Step c): Separation of the Counter Ion

To remove the perchlorate ions present in the reaction mixture, the solution is filtered through a column filled with 50 g of ion exchanger Lewatit M500 OH. The ion exchanger is loaded with hydroxide ions, so that during the filtration perchlorate ions are removed from the solution and are replaced by hydroxide ions.

Step d): Dispersing of the Particles in the Matrix Monomer 90 g of a mixture of bis-GMA and TEG-DMA with a mixing ratio of 1:1 are added to the reaction solution ion-exchanged in step c).

Step e): Processing of the Reaction Solution

Volatile components ammonia, ethanol, and water present in the solution are removed from the mixture by vacuum distillation on a rotary evaporator. What remains is a 10% dispersion of silanized $SiO_2$—BaO nanoparticles with Bis-GMA/TEG-DMA as the matrix monomer.

EXAMPLE 3

Use of $Ba(OH)_2$ as a BaO Precursor

Steps a) and b): Particle Synthesis and Silanization

Solution A: 220 ml of ethanol are provided in a reaction vessel, and first 12.3 ml of tetraethyl orthosilicate and 13.1 ml of 3-methacryloxypropyltrimethoxysilane (MPTMS) are added with stirring, and then 1.4 ml of methacrylic acid is added to stabilize the solution. Finally, 71.5 ml of saturated barium hydroxide solution (i.e. 4.6% aqueous $Ba(OH)_2$ solution) is added to the mixture, likewise under stirring.

Solution B: 256 ml of ethanol are mixed with 85 ml of a 2 molar $NH_3$ solution in ethanol.

To start the reaction, solution B is rapidly added to solution A with vigorous stirring. Subsequently, the reaction mixture is stirred for 24 h. As a result of particle formation, the solution gradually becomes turbid.

Step c): Separation of the Counter Ion

To remove the methacrylate ions present in the reaction mixture, the solution is filtered through a column filled with 50 g of ion exchanger Lewatit M500 OH. The ion exchanger is loaded with hydroxide ions, so that during the filtration methacrylate ions are removed from the solution and are replaced by hydroxide ions.

Step d): Dispersing of the Particles in the Matrix Monomer 40 g of a mixture of bis-GMA and TEG-DMA with a mixing ratio of 1:1 are added to the reaction solution ion-exchanged in step c).

Step e): Processing of the Reaction Solution

Volatile components ammonia, ethanol, and water present in the solution are removed from the mixture by vacuum distillation on a rotary evaporator. What remains is a 20% dispersion of silanized $SiO_2$—BaO nanoparticles with Bis-GMA/TEG-DMA as the matrix monomer.

EXAMPLE 4

Synthesis of a Commercialized System Including $SiO_2$ Particles, as a Comparative Example A commercially available sol of 50 wt % of SiO$_2$ in TEG-DMA is mixed with bis-GMA in a 2:1 ratio. The resulting dispersion has a solids content of 33%.

EXAMPLE 5

Polymerization of the Nano-Composites

The dispersions obtained in Examples 1 to 4 are mixed with a mixture of camphorquinone and ethyl dimethylaminobenzoate, and then are cured under UV light. Subsequently, the optical properties of the cured, i.e. polymerized, composites are determined on a Hunterlab Colorquest colorimeter. The results are shown in Table 1.

TABLE 1

Summary of optical properties

| Example | Solids content [wt %] | Transparency [%] | Translucency [%] | X-ray opacity of filler material [% Al] |
|---|---|---|---|---|
| 1 | 10 | 78.4 | 61.8 | 73.5 |
| 2 | 10 | 91.4 | 83.0 | 114.2 |
| 3 | 20 | 88.5 | 86.6 | 107.5 |
| 4 | 33 | 88.2 | 73.8 | 35.5 |

What is claimed is:

1. A dispersion suitable for use as a precursor for a dental composite, comprising: a filler material and a matrix monomer having at least one polymerizable group, the filler material comprising nanoscale mixed oxide particles that are sterically stabilized by a sol stabilizer, the nanoscale mixed oxide particles including silicon, at least one metal M having an atomic number Z >36 in oxidic form, and at least one covalently bound polymerizable group that is copolymerizable with the at least one polymerizable group of the matrix monomer, wherein the nanoscale mixed oxide particles including the silicon and the metal M have a formula: SiO$_2$-MO$_x$ and/or SiO$_2$-MO$_x$-M'O$_y$, where M' is a metal having an atomic number Z >36 in oxidic form, wherein the nanoscale mixed oxide particles further comprising at least one further organic group covalently bound thereto.

2. The dispersion as in claim 1, wherein the nanoscale mixed oxide particles have a spherical shape.

3. The dispersion as in claim 1, wherein the matrix monomer is at least one acrylate selected from a group comprising methyl, ethyl, butyl, benzyl, furfuryl, and phenyl (meth)acrylate, bisphenol A di(meth)acrylate, bis-GMA, ethoxylated bisphenol A di(meth)acrylate, UDMA, di-, tri-, and tetraethylene glycol di(meth)acrylate, trimethylolpropane tri(meth)acrylate, pentaerythritol tetra(meth)acrylate, butanediol di(meth)acrylate, 1,10-decanediol di(meth)acrylate, 1,12-dodecanediol di(meth)acrylate, and mixtures thereof.

4. The dispersion as in claim 1, wherein the metal M is an element selected from the group consisting of Ba, Sr, La, Cs, Sn, Zr, Yb, Y, Ta, Ce, Pr, Nd, Sm, Eu, Gd, Tb, Dy, Ho, Er, Tm, Lu, Bi, and combinations thereof.

5. The dispersion as in claim 1, wherein the filler material has an average particle size ranging from 5 to 100 nm.

6. The dispersion as in claim 1, wherein the at least one covalently bound polymerizable group of the filler material is selected from the group consisting of an acrylate group, a methacrylate group, and a 3-methacryloxypropyl (MPTM) group.

7. The dispersion as in claim 1, wherein the filler material is present in a content from 10 to 70 wt %.

8. The dispersion as in claim 1, wherein the filler material is present in a content from 30 to 50 wt %.

9. The dispersion as in claim 1, wherein the at least one further organic group is selected from the group consisting of an organic side chain and an alkyl group.

10. The dispersion as in claim 1, wherein the filler material has a refractive index that differs from a refractive index of the matrix monomer by less than 0.1.

11. A dental composite obtained by curing the dispersion according to claim 1.

12. The dental composite as in claim 11, wherein, at a content of filler material of at least 10 wt %, translucency for light of a wavelength from 400 to 750 nm is at least 30% and/or transparency for light of a wavelength from 400 to 750 nm is at least 75%.

13. The dental composite as in claim 11, wherein the nanoscale mixed oxide particles have an X-ray opacity from 50 to 15,000%Al.

14. A method for preparing a dental composite using a dispersion as a precursor, the precursor comprising a nanoscale mixed oxide having at least one polymerizable group, as a filler material, and a matrix monomer, and is obtained by preparing a sol, and subsequently curing the precursor, comprising the steps of:
   a) preparing nanoscale mixed oxide particles of SiO$_2$ and an X-ray opaque metal oxide of a metal M starting from at least one silicon precursor and a metal salt M$_a$X$_b$ or a metal hydroxide M$_a$(OH)$_b$, the metal hydroxide being at least partially neutralized by adding an organic acid HA;
   b) functionalizing the mixed oxides prepared in step a);
   c) removing a counter ion X or conjugate base of the organic acid used in step a) from the reaction solution;
   d) dispersing the filler particles functionalized in step b) in the matrix monomer;
   e) processing the dispersion; wherein
   first, in step a), a solution A and a solution B are provided, wherein solution A includes a solvent, an organic silicon precursor, and an X-ray opaque metal M in form of a salt or as a hydroxide, and solution B includes a solvent and an aqueous base, and wherein solution A or solution B further includes a sol stabilizer, and wherein solution B and solution A are mixed under stirring, and the reaction solution is stirred to complete formation of particles;
   wherein subsequently, in step b), a silane having a polymerizable group is added for functionalizing; and
   wherein in step e) solvents, water and base are removed.

15. The method as in claim 14, wherein steps a) through e) are performed as a one-pot synthesis.

16. The method as in claim 14, wherein in step a) particles form in self-organizing manner.

17. The method as in claim 14, wherein a silane of the formula SiX$_4$ is used as the silicon precursor in solution A, the silane including 4 hydrolyzable groups X selected from a group of X=OR, halogen, NR$_2$ (R=alkyl, aryl), H, a tetraalkoxysilane selected from a group comprising tetramethylorthosilicate (TMOS) having a formula Si(OCH$_3$)$_4$, tetraethylorthosilicate (TEOS) having a formula Si(OC$_2$H$_5$)$_4$, tetrapropoxysilane having a formula Si(OC$_3$H$_7$)$_4$; and/or a silane of the formula RSiX$_3$, including 3 hydrolyzable groups X selected from a group of X=OR, halogen, NR$_2$ (R=alkyl, aryl), H, and a non-hydrolyzable organic side group R, wherein R is an alkyl or aryl.

18. The method as in claim 14, wherein a further metal salt M$^T_c$X$_b$ or a hydroxide of an X-ray opaque metal M$^T$ is added to solution A.

19. The method as in claim 14, wherein the metal M and/or the metal $M^T$ comprise barium or strontium.

20. The method as in claim 14, wherein barium and/or strontium perchlorate is employed as the metal salt.

21. The method as in claim 14, wherein barium and/or strontium hydroxide is employed as the metal hydroxide.

22. The method as in claim 14, wherein a low boiling alcohol is employed as a solvent in solutions A and B, the low boiling alcohol being selected from a group consisting of ethanol, methanol, and isopropanol.

23. The method as in claim 14, wherein a sterically demanding silane and/or a protective colloid is employed as a sol stabilizer in solution A or B.

24. The method as in claim 14, wherein step b) additionally uses a silane having an organic non-copolymerizable residue, the silane having a formula $RSiX_3$ or $RR^TSiX_2$, including hydrolyzable groups X selected from a group of X=OR, halogen, $NR^{T1}_2$, with $R^{T1}$=alkyl, aryl, and non-hydrolyzable organic residues R and/or $R^T$.

25. The method as in claim 14, wherein in step c) the counter ion X of the metal salt or the conjugate base of the organic acid used in step a) is replaced by hydroxide ions using an ion exchanger.

26. The method as in claim 14, wherein a methacrylate is employed as the matrix monomer, the methacrylate being selected from a group consisting of methyl, ethyl, butyl, benzyl, furfuryl, and phenyl (meth)acrylate, bisphenol A di(meth)acrylate, bis-GMA, ethoxylated bisphenol A di(meth)acrylate, UDMA, di-, tri-, and tetraethylene glycol di(meth)acrylate, trimethylolpropane tri(meth)acrylate, pentaerythritol tetra(meth)acrylate, butanediol di(meth)acrylate, 1,10-decanediol di(meth)acrylate, 1,12-dodecanediol di(meth)acrylate, and mixtures thereof.

27. The method as in claim 14, wherein the dispersion is transformed into the dental composite by irradiating light of an appropriate wavelength.

* * * * *